USOO5104792A

United States Patent [19]

Silver et al.

[11] Patent Number: 5,104,792

[45] Date of Patent: Apr. 14, 1992

[54] METHOD FOR AMPLIFYING UNKNOWN NUCLEIC ACID SEQUENCES

[75] Inventors: Jonathan Silver, Bethesda, Md.; Stephen Feinstone, Washington, D.C.

[73] Assignee: The United States of America as represented by the Department of Health and Human Services, Washington, D.C.

[21] Appl. No.: 454,171

[22] Filed: Dec. 21, 1989

[51] Int. Cl.⁵ .................. C12Q 1/68; C07H 15/12; C12N 15/00
[52] U.S. Cl. ........................... 435/6; 536/27; 935/77; 935/78
[58] Field of Search ............... 435/6; 536/27; 935/77, 935/78

[56] References Cited

U.S. PATENT DOCUMENTS 4,683,195  7/1987  Mullis et al. .................. 435/6

FOREIGN PATENT DOCUMENTS 0224126  3/1987  European Pat. Off. .

OTHER PUBLICATIONS

Sanger et al, J. Mol. Biol., vol. 143, 198, pp. 161–178.

Primary Examiner—Robert A. Wax
Assistant Examiner—Mindy B. Fleisher
Attorney, Agent, or Firm—Mishrilal Jain

[57] ABSTRACT

A modification of the PCR technique is described which allows fragments of RNA or DNA to be amplified without prior knowledge of their sequence. The technique can be used to amplify viral nucleic acids present in small amounts in clinical material allowing, for example, the diagnosis of a particular virus infection or the discovery of new viruses.

1 Claim, 2 Drawing Sheets

SCHEMATIC OF METHOD

FIRST ROUND OF RANDOM PRIMING:

SECOND ROUND OF RANDOM PRIMING:

SUBSEQUENT CYCLES OF PCR WITH NON-DEGENERATE OLIGO:

SCHEMATIC OF METHOD

"UNIVERSAL" PRIMER:

FIRST ROUND OF RANDOM PRIMING:

SECOND ROUND OF RANDOM PRIMING:

SUBSEQUENT CYCLES OF PCR WITH NON-DEGENERATE OLIGO:

METHOD FOR AMPLIFYING UNKNOWN NUCLEIC ACID SEQUENCES

The present invention is related generally to the methodology of nucleic acid amplification. More particularly, the present invention is related to the amplification of unknown RNA and DNA sequences using "universal" primers in conjunction with the polymerase chain reaction (PCR).

PCR (Mullis and Faloona, 1987, *Methods in Enzymology*, 155, 335) allows nucleic acid sequences up to a few kilobases in length to be amplified over $10^5$ fold in a few hours in vitro, but requires that the sequence at the ends of the nucleic acid be known in advance. On the other hand, random hexamers can be used to copy a nucleic acid fragment whose sequence is unknown, but this procedure leads to very minimal amplification, only a few fold (Feinberg and Vogelstein, 1983, *Anal Biochem* 132, 6). Thus, a generally applicable technique for multifold amplification of unknown nucleic acid sequences has not heretofore been described.

SUMMARY OF THE INVENTION

It is, therefore, an object of the present invention to provide a method for amplifying nucleic acid fragments without prior knowledge of their sequence provided only that the nucleic acid can be purified in advance.

The method makes use of a set of oligonucleotide (oligo) primers all of which share the same 5' end sequence for a distance long enough to serve as primer in a subsequent PCR reaction, vide infra, but whose 3' end sequences are multiply degenerate. These 3' degenerate oligos are referred to herein as "universal" primers and are used to prime essentially randomly any target RNA or DNA template. Two or more cycles of such "random" priming leads to copies of the target nucleic acid sequence "sandwiched" between the 5' fixed sequence of the "universal" primers and the reverse complement of this sequence. PCR is then performed using nondegenerate oligo primers containing the 5' fixed sequence without the 3' degenerate sequence. Additional sequences may be appended to the 5' end of the nondegenerate primers to facilitate insertion into a cloning vector or to add other functionally useful sequences.

It is a further object of the present invention to amplify nucleic acids from virus particles present in minute amounts in biological samples, without first knowing the sequence of any such virus, thereby facilitating diagnosis of viral infection and identification of a particular virus.

Another object of the present invention is to provide a method for amplifying and cloning new viruses, thereby facilitating their discovery. In genetics, the technique could be used to amplify nucleic acid fragments obtained in minute amounts from particular chromosome locations by microchromosome dissection.

Other objects and advantages will become evident from the following detailed description of the invention.

BRIEF DESCRIPTION OF THE DRAWINGS

These and other objects, features and many of the attendant advantages of the invention will be better understood upon a reading of the following detailed description when considered in connection with the accompanying drawings wherein.

DETAILED DESCRIPTION OF THE INVENTION

Figure 1:
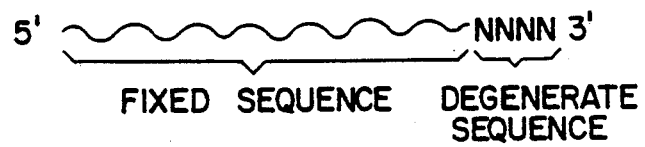
FIG. 1 is a schematic representation of the strategy of PCR using "universal" primers. The unknown nucleic acid sequence to be amplified is indicated by a solid line. The "universal" primer is indicated by a wavy line terminating in NNNN. The wavy line portion designates a fixed, though arbitrary, sequence at the 5' end, and the N's indicate multiple degeneracy at the 3' end. While the particular embodiment described herein uses a set of "universal" primers containing all possible sets of bases in the last four positions at the 3' end (hence the designation "NNNN"), a different number of degenerate bases could be used, and they need not be completely degenerate (i.e., less than all possible bases need be present in any position). Dotted lines indicate newly synthesized DNA made with an appropriate DNA polymerase copying the target nucleic acid sequence by extending the annealed "universal" primers.
Figure 1:
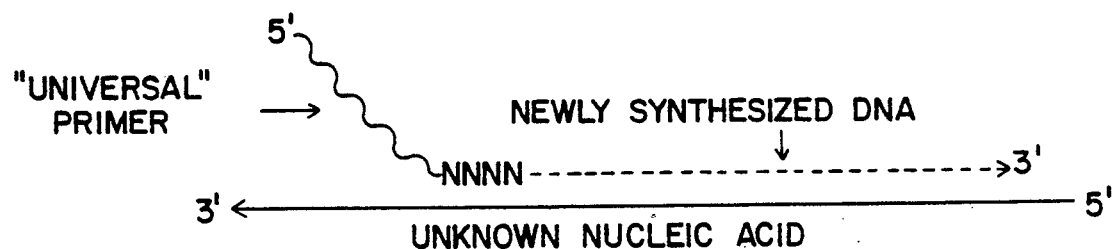
Figure 1:
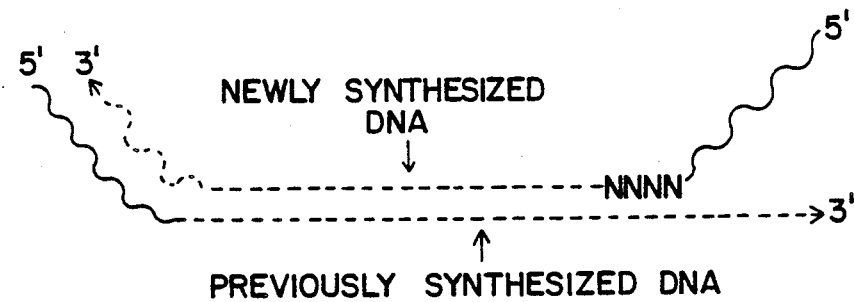
Figure 1:
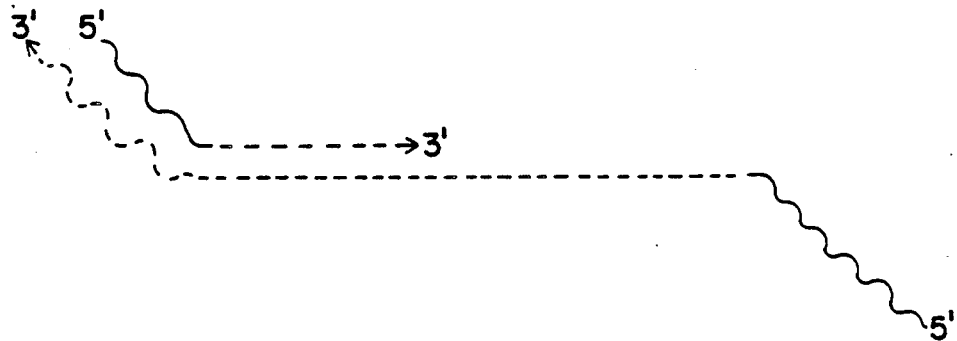
Figure 2:
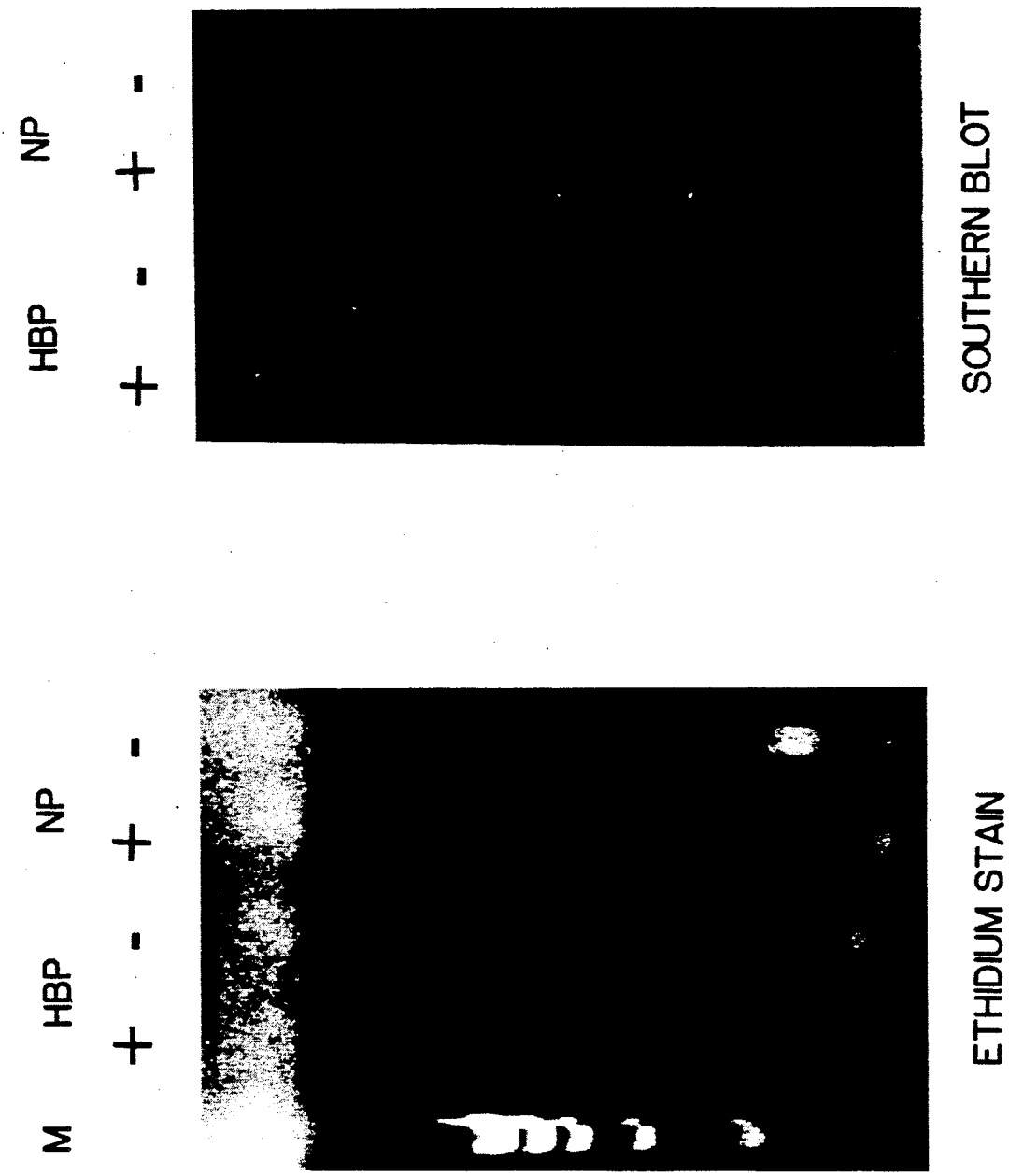
FIG. 2 shows the results of applying the method to amplifying DNA from the plasma of an individual infected with hepatitis B virus versus normal plasma. The left hand panel shows an ethidium bromide stained agarose gel containing the electrophoresed products of the amplification reaction from normal plasma (NP) or hepatitis B plasma (HBP). A "+" indicates that the plasma was treated with micrococcal nuclease to remove non-virion nucleic acid prior to "universal" primer PCR. Virion nucleic acid is protected from micrococcal nuclease digestion by the viral capsid protein. "−" indicates that the micrococcal nuclease was omitted. The right hand panel shows a Southern blot of the gel shown on the left, after hybridization to a hepatitis B viral DNA probe.

The above and various other objects and advantages of the present invention are achieved by a method of DNA amplification, comprising:

(a) purifying the target nucleic acid to be amplified;

(b) annealing to the target nucleic acid a collection of oligonucleotide primers, called "universal" primers, all of which have the same 5' end sequence for a distance sufficient to serve as primer in a subsequent PCR reaction, but which have different 3' end sequences;

(c) performing two or more rounds of primer extension of the annealed "universal" primers using a DNA polymerase appropriate for the target, such as a reverse transcriptase if the target is RNA or DNA or unknown, or Klenow fragment of *E. coli* DNA polymerase if the target is DNA;

(d) removing the 3' degenerate "universal" oligos;

(e) amplifying by PCR, using an oligo whose sequence is the same as the fixed 5' end sequence of the "universal" primers, that is without their 3' end degenerate bases;

(f) detecting and characterizing the amplified material obtained from step (e) by standard techniques such as gel electrophoresis, Southern blot, hybridization of immobilized amplified DNA to defined probes, labelling of the amplified DNA for use as probe in hybridization to immobilized potential target nucleic acids ("reverse" blot), cloning, sequencing, or other standard molecular biological techniques well known to one of ordinary skill in the art.

It may be pointed out here that if the template is RNA, at least the first round of primer extension with the universal oligos must be performed with a polymerase capable of copying RNA, such as reverse transcriptase.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated by reference. Unless mentioned otherwise, the techniques employed or contemplated herein are standard methodologies well known to one of ordinary skill in the art. The embodiments are only illustrative and not limiting.

MATERIALS AND METHODS

Unless mentioned otherwise, all chemicals, reagents and the like were of analytical grade and obtained from commercial sources.

Micrococcal nuclease and Klenow enzyme were obtained from Boehringer Mannheim. Taq polymerase was obtained from Cetus-Perkin Elmer. Oligonucleotides were synthesized on an Applied Biosystems Model 380B and purified by ethanol precipitation. PCR was performed in a Cetus-Perkin Elmer Thermocycler.

To test the feasibility and reliability of the method, the technique of the present invention was applied to amplifying DNA from the plasma of an individual with hepatitis B infection versus normal plasma. The hepatitis B plasma came from a chronic carrier. Blood was collected in standard citrate solution to prevent clotting. To eliminate non-viral nucleic acids, 5 ml of each plasma was treated with 700 units of micrococcal nuclease for 1 hour at 37° C. in the presence of $CaCl_2$ added to make the mixture 25 mM in $CaCl_2$ (not counting the Ca originally present in the plasma); 50 units of heparin was also added to prevent clotting. Control tubes were not treated with micrococcal nuclease to determine the need for this step (see below). The micrococcal nuclease was then inactivated by adding EGTA to 27.5 mM, and 3.5 ml of the treated plasma was spun through 1 ml of 20% sucrose in an SW60 rotor (Beckman) at 55,000 rpm for 2 hours to pellet the virus. It is noted that the additional purification obtained by pelleting the virus may or may not be necessary.

Viral nucleic acid was prepared by standard protocols (treatment with 50 $\mu$g/ml proteinase K in 1% SDS, followed by phenol-chloroform extraction and ethanol precipitation). Two rounds of modified "random" primer extension with "universal" primers were then performed in 50 $\mu$l volumes with 2.5 units of Klenow enzyme in 25 mM Tris-HCl pH 8.0, 2.5 mM $MgCl_2$, 5 mM 2-mercaptoethanol, 100 mM Hepes-HCl pH 6.6 and 4 $\mu$M "universal" oligonucleotides with the sequence 5'CAGTGACCTGTCTTGGACTCNNNN 3' where N indicates A, C, G, or T, in equal proportions. Each round of primer extension was for 1 hour at 42° C. and the rounds were separated by heat denaturation at 94° C. for 1 minute followed by addition of 2.5 units of fresh Klenow enzyme. The reaction mixtures were centrifuged through G-50 spin columns to reduce the concentration of degenerate oligonucleotides. The flow through from the G-50 spin columns was ethanol precipitated. An aliquot of the ethanol precipitate was then used as a template in a PCR containing 2.5 units of Taq polymerase in 100 $\mu$l of 10 mM Tris-HCl pH 8.3, 2.5 mM MgCl, 50 mM KCl, 0.01% gelatin, 200 $\mu$M each dNTP, and 1 $\mu$M oligonucleotide with the sequence 5'TCAGAATTCAGTGACCTGTCTTGGACTC 3'. Cycling conditions were 94° C. for 1'30", 48° C. for 1'30", 72° C. for 3' for 30 cycles. For analysis, 10 $\mu$l of the amplified material was electrophoresed in a 1% agarose gel (FIG. 1A), transferred to nitrocellulose by Southern blotting, and hybridized to a full length hepatitis B virus probe (FIG. 1B). The results showed that treatment with micrococcal nuclease was sufficient to remove amplifiable DNA from normal plasma, and that the "universal" primer PCR method was successful in amplifying hepatitis B DNA from the patient plasma.

If it were not known in advance which virus was likely to be present in a clinical specimen, then an alternative analytical procedure would be to label the PCR amplified material with $P^{32}$, biotin, or other standard label, and use this labelled material as a probe in hybridization to a Southern blot containing a set of possible target viruses immobilized on a filter. Such a "reverse blot" procedure has been employed for the identification of major histocompatibility alleles amplified by PCR. Of course, the technique described herein can be modified to amplify nucleic acid sequences from RNA as well as DNA viruses, by using reverse transcriptase instead of Klenow enzyme during the "random" primer steps.

The oligonucleotides used to perform "universal" primer PCR are, of course, not limited to those used herein. Further modification in the method may be made by varying the length and content of the 3' degenerate ends of the "universal" primers, as well as their 5' fixed portion. Additional obvious modifications include using different DNA polymerases and altering the temperature at which the modified random priming is performed. These modifications would affect the completeness of copying the template nucleic acid and the average length of the copied segments. Given the principles and the examples provided herein, such modifications are easily suggested to one of ordinary skill in the art.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method for performing polymerase chain reaction (PCR) on nucleic acid fragments of unknown sequence, comprising the sequential steps of:
   (a) obtaining purified template RNA or DNA to be amplified;
   (b) annealing to template RNA or DNA universal primers whose 5' ends have a fixed sequence of sufficient length to serve as a primer in a subsequent polymerase chain reaction, and whose 3' ends are degenerate for random priming of the template;
   (c) extending the universal primers by two or more rounds of primer extension with a polymerase capable of copying a RNA or a DNA template;
   (d) removing the 3' degenerate oligonucleotides;
   (e) amplifying with PCR using primers whose 3' sequence is the same as the fixed 5' portion of the universal oligonucleotides;
   (f) then identifying the PCR product obtained from step (e) by standard molecular biological techniques.

* * * * *